United States Patent
Vaickus

(10) Patent No.: US 12,057,229 B1
(45) Date of Patent: Aug. 6, 2024

(54) SYSTEM AND METHOD FOR ANALYZING CYTOLOGICAL TISSUE PREPARATIONS

(71) Applicant: Dartmouth-Hitchcock Clinic, Lebanon, NH (US)

(72) Inventor: Louis J. Vaickus, Etna, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 607 days.

(21) Appl. No.: 16/679,133

(22) Filed: Nov. 8, 2019

Related U.S. Application Data

(60) Provisional application No. 62/757,225, filed on Nov. 8, 2018.

(51) Int. Cl.
*G16H 50/20* (2018.01)
*G01N 15/1433* (2024.01)
(Continued)

(52) U.S. Cl.
CPC ......... *G16H 50/20* (2018.01); *G01N 15/1433* (2024.01); *G06F 18/2148* (2023.01); *G06F 18/41* (2023.01); *G06N 3/08* (2013.01); *G16H 30/40* (2018.01); *G01N 2015/1006* (2013.01); *G06V 2201/03* (2022.01)

(58) Field of Classification Search
None
See application file for complete search history.

(56) References Cited

U.S. PATENT DOCUMENTS

| 5,544,650 A * | 8/1996 | Boon .................. G06V 20/693 382/133 |
| 5,889,880 A | 3/1999 | Doerrer |

(Continued)

FOREIGN PATENT DOCUMENTS

WO WO-2009151610 A2 * 12/2009 ........... G01N 15/147

OTHER PUBLICATIONS

Grala, Bartlomiej, et al. "New Automated Image Analysis Method for the Assessment of Ki-67 Labeling Index in Meningiomas." Folia Histochemica et Cytobiologica 47.4 (2009): 587-92. ProQuest. Web. Jan. 22, 2024. (Year: 2009).*

(Continued)

*Primary Examiner* — Lena Najarian
(74) *Attorney, Agent, or Firm* — Loginov & Associates, PLLC; William A. Loginov

(57) ABSTRACT

A system and method for delivering diagnostic information to a user in an automated manner. An image processing module reads magnified raw image data from whole slides containing tissue cells. A background deletion process identifies and isolates cell images. A neural network, which is trained based upon image data, classifies the cell images. The classification uses specialist criteria to categorize/segment the cell images into a plurality of discrete cell types. A display process provides the diagnostic information to the user. The neural network can be trained using a plurality of cell types each having the specialist criteria. The diagnostic information includes filtered and/or reorganized images of the tissue cells. Additionally, the user can request the diagnostic information based upon an account that provides payment according to a predetermined formula associated with at least one of a type, format, and timing of information delivered to the user.

5 Claims, 13 Drawing Sheets

(51) Int. Cl.
*G06F 18/214* (2023.01)
*G06F 18/40* (2023.01)
*G06N 3/08* (2023.01)
*G16H 30/40* (2018.01)
*G01N 15/10* (2006.01)

(56) References Cited

U.S. PATENT DOCUMENTS

| | | | |
|---|---|---|---|
| 5,933,519 | A | 8/1999 | Lee |
| 8,744,213 | B2 | 6/2014 | Tatke |
| 10,371,929 | B2 | 8/2019 | Hulsken |
| 10,507,082 | B2 | 12/2019 | Elsner |
| 2001/0018659 | A1* | 8/2001 | Koritzinsky ............ G16H 30/40 705/3 |
| 2008/0166035 | A1* | 7/2008 | Qian .................... G06V 20/698 382/133 |
| 2009/0319291 | A1* | 12/2009 | Noordvyk .............. G16H 50/20 705/2 |
| 2012/0034647 | A1* | 2/2012 | Herzog .............. G01N 21/6458 435/288.7 |
| 2014/0235487 | A1* | 8/2014 | McDevitt ............... G16H 50/30 702/19 |
| 2015/0374306 | A1* | 12/2015 | Gelbman ............. G06V 40/171 600/476 |
| 2016/0042511 | A1* | 2/2016 | Chukka ................ G06T 7/0012 382/133 |
| 2016/0272934 | A1* | 9/2016 | Chander ................ C12M 47/04 |
| 2017/0169567 | A1* | 6/2017 | Chefd'Hotel ........ G06N 3/0454 |
| 2018/0232883 | A1* | 8/2018 | Sethi .................... G06K 9/6267 |

OTHER PUBLICATIONS

Anderlini et al., "Automated urinalysis with expert review for incidental identification of atypical urothelial cells: An anticipated bladder carcinoma diagnosis", Clinica Chimica Acta 451 (2015) 252-256.

Pantazopoulos et al., "Static cytometry and neural networks in the discrimination of lower urinary system lesions", Urology 51:946-950, 1998.

Bioview, "Automated imaging & analysis appication for the identification of urothelial carcinoma cells", https://bioview.com/applications/cytology/urine-cytology/.

Moonen et al., "Quantitative cytology on bladder wash versus voided urine: a comparison of results", European Urology 49 (2006) 1044-1050.

Pouliakis et al., "Artificial neural networks as decision support tools in cytopathology: past, present, and future", Biomedical Engineering and Computational Biology 2016:7 pp. 1-18.

Pantazopoulos et al., "Comparing neural networks in the discrimination of benign from malignant lower urinary tract lesions", British Journal of Urology (1998) 81, 574-579.

Pantazopoulos et al., "Back propagation neural network in the discrimination of benign from malignant lower urinary tract lesions", The Journal of Urology, vol. 159, 1619-1623, May 1998.

Vriesema et al., "Neural network-based digitized cell image diagnosis of bladdere wash cytology", Diagnostic Cytopathology, vol. 23, No. 3.

Ciamac Moallemi, "Classifying Cells for Cancer Diagnosis Using Neural Networks," Special Feature, IEEE Expert, pp. 3-12, Dec. 1991, downloaded Sep. 2, 2020.

Myron R. Melamed, "Automated Urinary Cytology for Cancer Detection", National Institutes of Health, https://grantome.com/grant/NIH/R01-CA014134-16#panel-abstract, 2015, 5 pages.

* cited by examiner

SYSTEM AND METHOD FOR ANALYZING CYTOLOGICAL TISSUE PREPARATIONS

RELATED APPLICATION

This application claims the benefit of U.S. Provisional Application Ser. No. 62/757,225, filed Nov. 8, 2018, entitled SYSTEM AND METHOD FOR ANALYZING CYTOLOGICAL TISSUE PREPARATIONS, the entire disclosure of which is herein incorporated by reference.

FIELD OF THE INVENTION

This invention relates to cytology systems and methods for use in diagnosing conditions within the body.

BACKGROUND OF THE INVENTION

Urine cytological analysis is a significant volume stream in most hospital pathology departments. Every case of hematuria (blood in the urine) is followed by cytological examination which typically entails depositing the cellular components of urine onto a slide, fixing and staining the cells, and examining them microscopically, which is performed first by technologist with a pathologist then providing the final review. Diagnostic categories are assigned using two criteria, nuclear to cytoplasmic ratio (NC) and nuclear atypia of bladder lining cells (urothelial cells) according to guidelines published in the well-known Paris System for Urine Cytopathology. The higher the NC and the more atypical the nuclei, the more likely a patient is to have urothelial carcinoma. Currently the diagnostic process is labor intensive, and produces qualitative results which must be combined with other characteristics about the patient to decide what if any intervention is necessary.

The current Paris System has four (4) main diagnostic categories: negative for high grade urothelial carcinoma (HGUC), atypical, suspicious for HGUC and positive for HGUC (these outcomes can represent, respectively 80%, 10%, 5%, 5% of clinical volume in one example).

More generally, cytological tissue preparations are generated by three principle methods: voiding (urine, sputum, feces), exfoliation (pap smears, brushing) and aspiration (fine needle aspiration, percutaneous, radiology guided, endoscopic). With current technology the only lesions which cannot be routinely accessed via a cytological technique are those contained within the skull. Cytology is significantly less costly than surgical pathology owing to its mostly non-invasive nature as compared to traditional open surgical procedures. Additionally, it can be performed without anesthesia, refrigeration, antibiotics, etc., so it is an ideal technique for rural areas, disaster zones and disadvantaged regions of the world. Moreover, with the advent of personalized molecular therapies, samples are increasingly being obtained via fine needle aspiration as opposed to surgical biopsy.

Also by way of further background, pap smears are a similar specimen with very well-defined diagnostic criteria. Since the early 2000's most large medical centers have employed a semi-automated machine learning based pre-screening device known as the BD FocalPoint. This device examines slides and assigns them to risk quintiles. Low risk slides are directly signed-out without a pathologist ever seeing them. High risk slides are viewed by a pathologist. The advent of this device has allowed many labs to continue to operate with reasonable staffing levels by reducing pathologist volumes. No other such machine learning device exists in all of pathology. Use of such automated techniques in the field of cytology is therefore desirable.

SUMMARY OF THE INVENTION

This invention overcomes disadvantages of the prior art by providing a system and method for delivering diagnostic information to a user (for example, urine cytology information) in an automated manner. An image processing module reads magnified raw image data from whole slides containing tissue cells. A background deletion process identifies and isolates cell images. A neural network, which is trained based upon image data, classifies the cell images. The classification uses specialist criteria to categorize/segment the cell images into a plurality of discrete cell types. A display process then provides the diagnostic information to the user in a desired format. The neural network can be trained using a plurality of cell types that are identified to contain each of the specialist criteria in an iterative process. The diagnostic information includes at least one of filtered and reorganized images of the tissue cells. Additionally, the user can request the diagnostic information based upon an account that provides payment according to a predetermined formula associated with at least one of a type, format, and timing of information delivered to the user. The neural network and/or other computing resources used herein can be provided on a cloud-based computing environment. Also, the magnified raw image data can be provided by an image-sensor that receives light via a magnification optics. The specialists can add data to the training of the neural network using a variety of techniques including direct access to the computing environment via local user graphical interfaces.

BRIEF DESCRIPTION OF THE DRAWINGS

The invention description below refers to the accompanying drawings, of which.

DETAILED DESCRIPTION

I. System Overview

Figure 1:
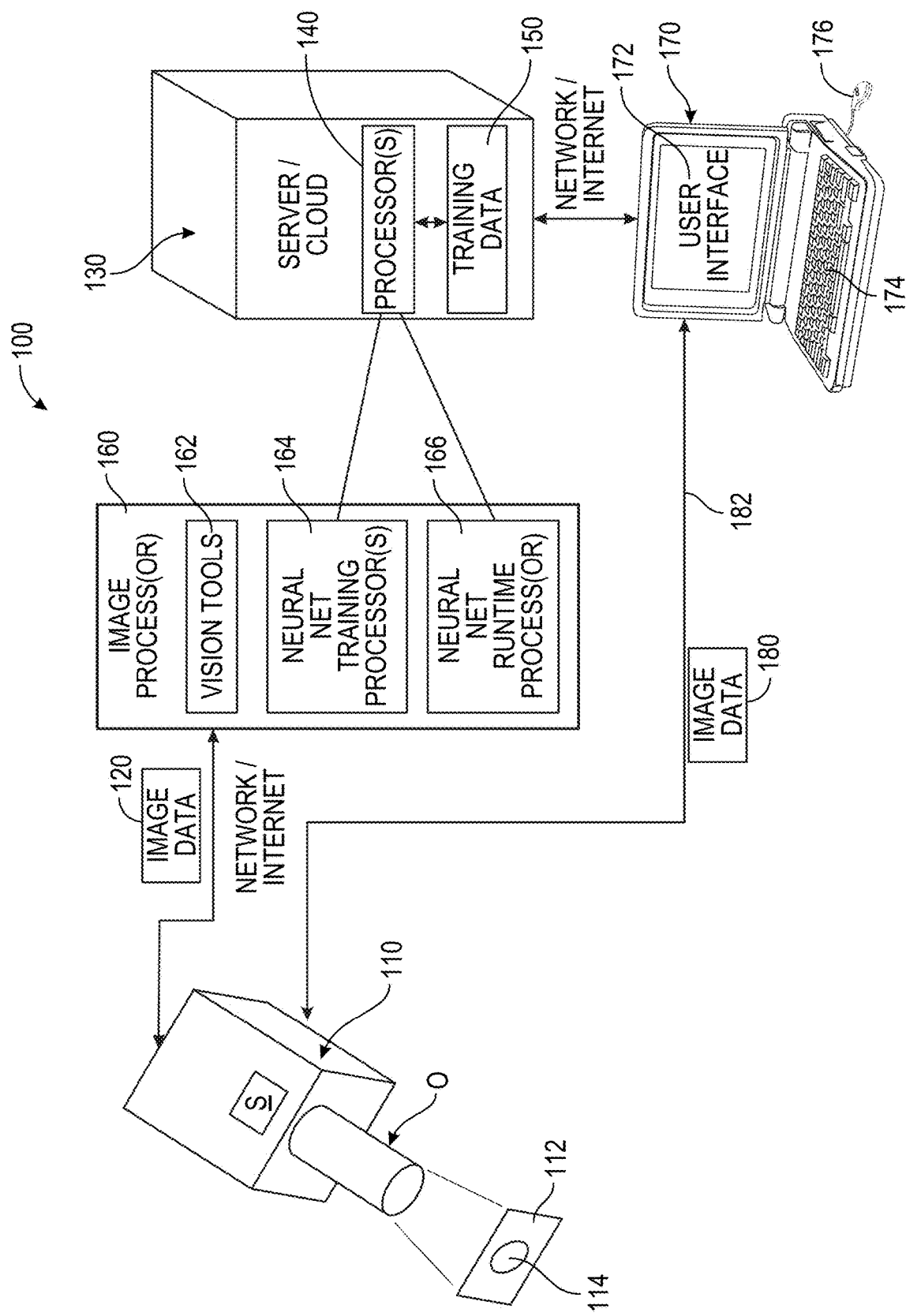
FIG. 1 is a diagram showing an exemplary arrangement for acquiring digital images of individual cells gathered from a patient using a cytological technique and provided to a process(or) that carries out the system and method herein to provide results to a user/clinician.

FIG. 1 shows a generalized arrangement 100 for carrying out the system and method herein. The arrangement 100 provides a user-based microscopic analysis system/device 110, that includes an image acquisition module of known construction, including an imaging sensor S that can convert received light, via magnifying optics O, from a slide or other surface 112 containing a cell smear 114, that can be prepared using conventional cytological techniques and substances from a human or animal subject.

The acquired, magnified image data 120 is stored and/or transmitted over a network (e.g. the Internet and/or a WAN/LAN) to a computing system 130 that can be instantiated in one or more servers and/or a cloud environment. The server/cloud system 130 includes one or more processors (that can be local and/or distributed 140, and associated data storage (that can be local and/or distributed) 150. As described below, the data 150 can consist of training data, based upon prior images and associated diagnosis. Other data can also be stored as appropriate to carry out the functions of the system and method.

The processor(s) 140 carry out an associated image process 160 that can include the various functional modules described hereinbelow. One module includes vision tools 162, which can be a variety of edge detectors, color analyzers, blob analyzers and other commercially available machine vision applications used to resolve objects within an image and apply pattern recognition thereto.

The process(or) 160 further includes a neural net/deep learning-based training process(or) 164 that carries out various training tasks and steps as described below, including the identification and classification of expert-based image data on various cell conditions in an overall library of cell images.

Additionally, the process(or) 160 includes a neural net/deep learning-based runtime process(or) 166 that applies the training data and associated classifiers to the acquired image data of a slide 112 to determine associated diagnostic data.

A user interface device 170, in the form of a computer, having a screen/touchscreen 172, keyboard 174, mouse 176, etc. is shown linked to the server/cloud 130 via an appropriate network, such as the Internet, LAN or WAN. This device 170 can be any acceptable data handling appliance, such as a smartphone, tablet, laptop, PC or server, and is capable of manipulating (e.g.) web page information that can be used to communicate with the cloud/server and associated processes/modules. This device 170 can be one of many, used by clinicians and other interested parties, who desire to obtain diagnostic data from the system and method. The computing/interface device 170 can also facilitate upload of local image data 180 of slides via a link 182 with the microscope/acquisition device 110.

II. Training and Runtime Process

By way of further background, while traditional cytological "smears" are still prepared (tissue is spread on a slide in a thin layer), laboratories are increasingly using liquid base preparatory techniques (LBP). LBP produces a randomly distributed sampling of the cellular components in a given sample and deposits them in an evenly dispersed monolayer. This makes analysis easier on the pathologists and cytotechnologists. LBP has the added benefit of producing slides which are ideal for acquiring images that can be processed using a deep learning neural network in accordance with the system and method herein.

Briefly, when LBP is scanned to a whole slide image (WSI), the resulting image contains randomly distributed cells separated by distinct background pixels. This allows for the automated tabulation of cell subimages into an organized dictionary containing A) the subimages, B) individual statistics of each cell subimage. These subimages can be manually classified by expert pathologists and used to train neural networks to, for instance, provide a risk score for a given cell ranking the likelihood that it is malignant, HPV-infected, etc. The input of trained neural networks to the generated dictionary of cells and statistics, can add subjective parameters (cell type, atypia score, etc).

This allows one to perform A) pancellular statistical analysis of the specimen (currently impossible due to the constraints of human operators), B) WSI filtering (e.g. removing all irrelevant objects from the original WSI, FIG. 2), C) WSI reconstruction (filtering and rearranging the original WSI to a more efficient format. The procedure of the system and method herein works for any LBP specimen (urine, paps, CSF, thyroid aspiration, etc.), and is contemplated to operate with other traditional smears that are generally free of significant non-cellular background material (i.e. blood, mucus, etc.). Also as shown, processes herein can be readily instantiated in a cloud-based computing environment (130), thereby allowing users to upload their WSI, review available statistics and image post-processing options and download the results via a user interface device (170).

Figure 2:
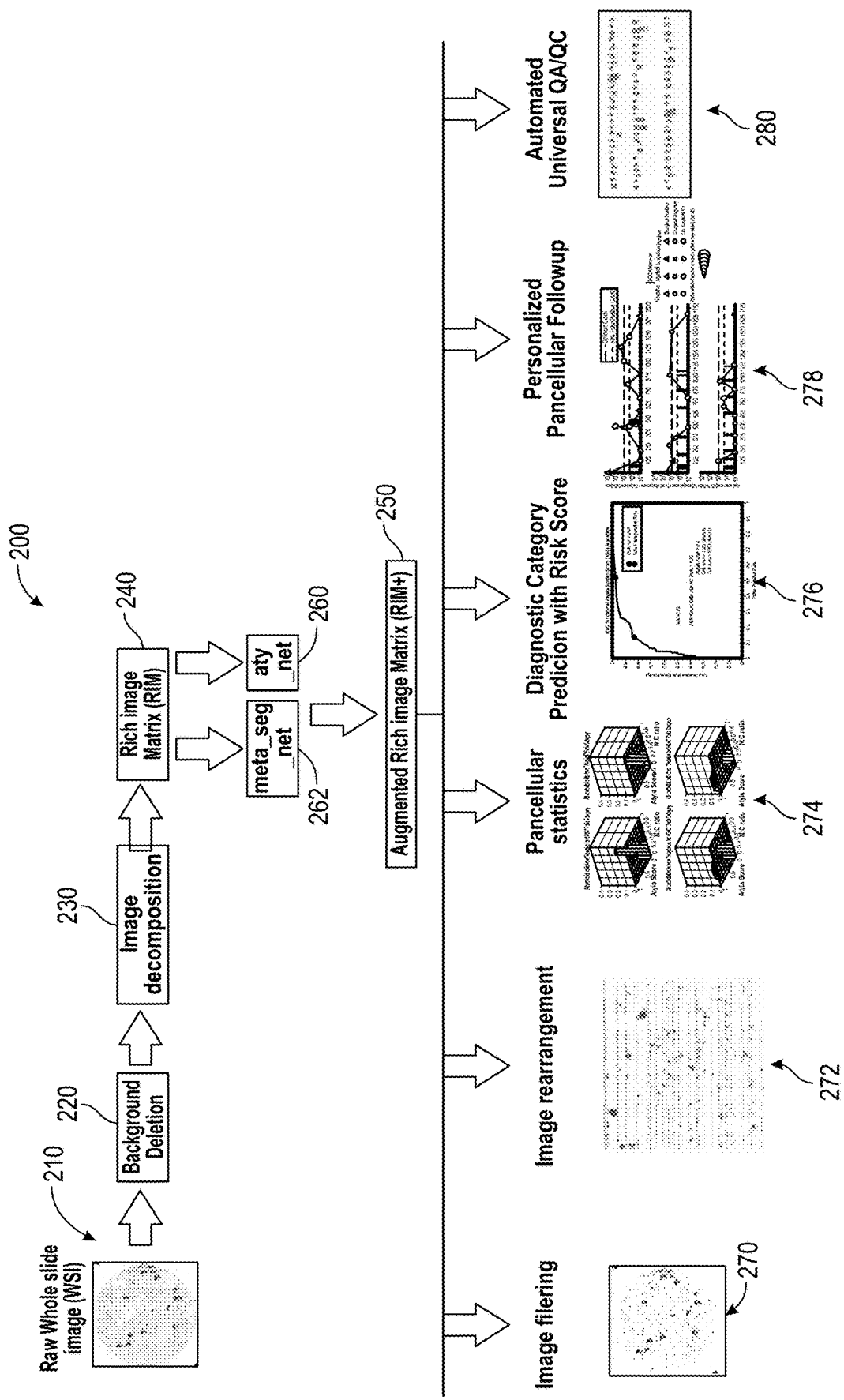
FIG. 2 is a flow diagram showing an overall procedure for acquiring images from whole slides, decomposing images of individual cells in the acquired images, creating a Rich Image Matrix (RIM), processing the RIM using a trained neural network to generate an augmented RIM (RIM+) and manipulating the RIM+ to generate results that can be accessed and analyzed by an end user, according to the system and method herein.

Reference is now made to FIGS. 2-7, which depict the overall process (FIG. 2) and various sub-processes (FIGS. 3-7) therein. As shown in FIG. 2, the procedure 200 acquires whole slide images 210 of cytology specimens as input. It removes/deletes background imagery (step 220) using vision tools (162) and then decomposes the images (step 230) into individual cell subimages, and creates a library of each subimage as well as a number of statistics including cell area, location in original image, perimeter, etc. This object is called a Rich Image Matrix (RIM) 240. Every cell in a given RIM is then processed by a library, aty_net 260 and meta_seg_net 262 to calculate subjective measures such as cell type and atypia score and objective measures such as nuclear to cytoplasmic ratio (NC ratio). These parameters are added to the RIM to create an Augmented RIM (RIM+) 250. The RIM+ object 250 can then be used for a number of manipulations including, image filtering 270, image reorganization/rearrangement 272, pancellular statistical analysis 274 (for example, using comparative 3D bargraphs), diagnostic category prediction 276, personalized pancellular follow-up 278 and universal automated quality analysis/quality control (QA/QC) 280, (e.g.) screening all cases signed out as benign for unrecognized malignancy.

Figure 3:
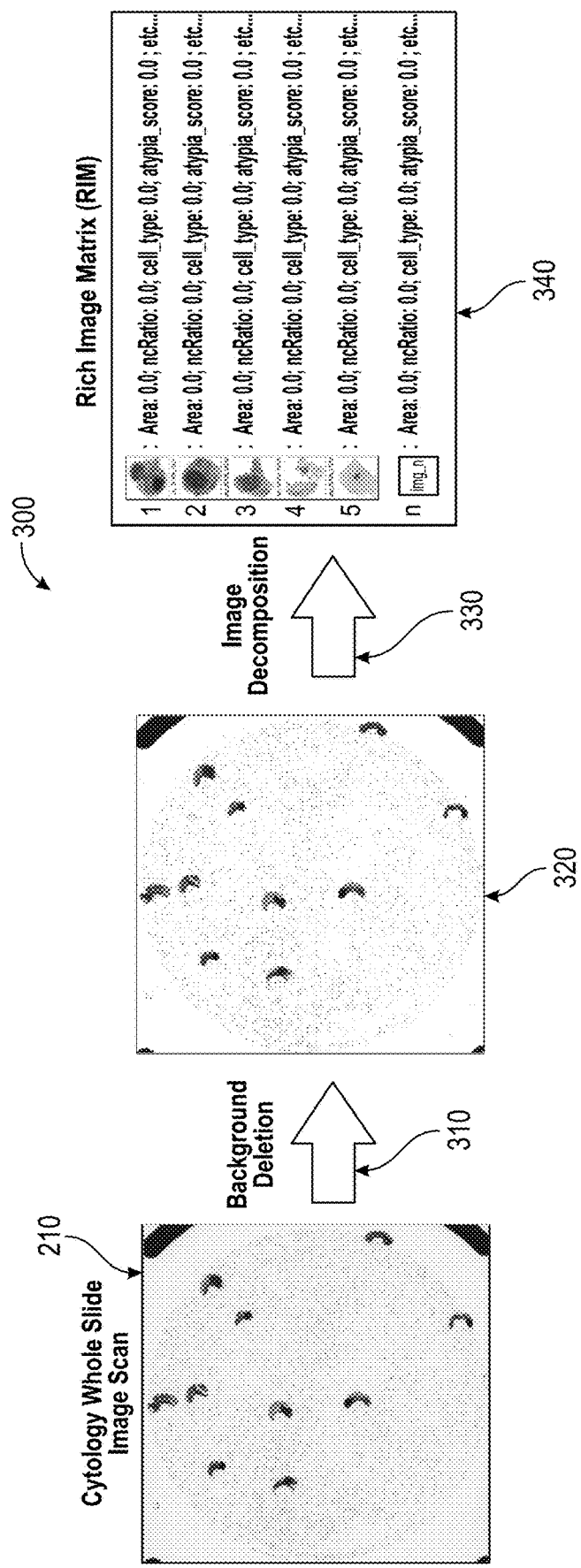
FIG. 3 is a flow diagram showing an image decomposition process to generate a Rich Image Matrix (RIM) according to FIG. 2.

With more particular reference to FIG. 3, a procedure 300 for background deletion and cell identification is shown. The above-described cytology slide image 210 is input by the user. A preprocessing procedure 310 uses thresholding to set (delete) background pixels to pure white (background-deleted image 320). It then identifies all contiguous objects separated by white pixels via image decomposition 330, these are the "cells". A dictionary 340 of every individual cell along with dozens of statistics (cell area, perimeter, average color intensity, location in original image, etc.) is created and tabulated in the process. This depicted dictionary/object 340 is the Rich Image Matrix (RIM).

Figure 4:
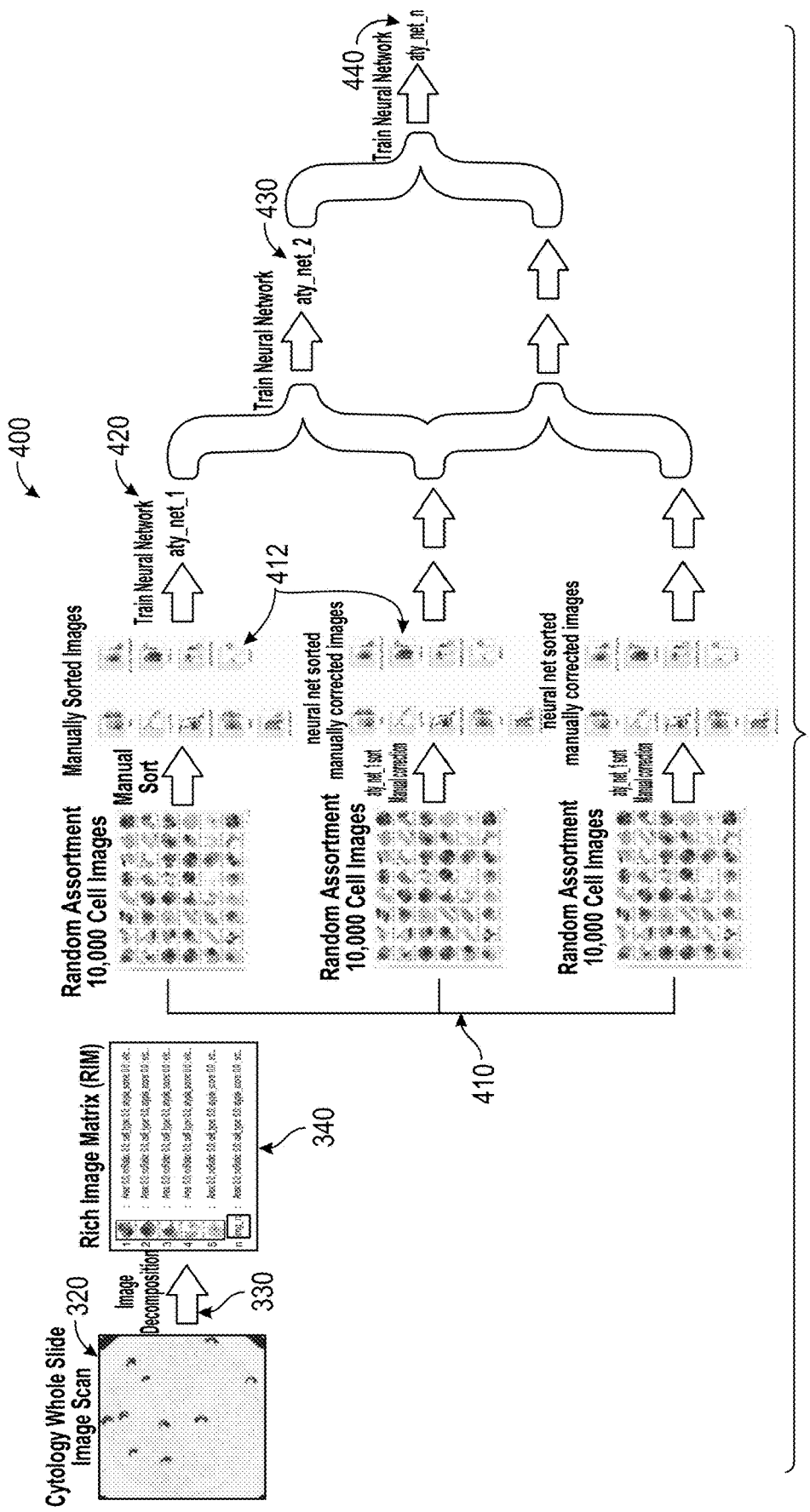
FIG. 4 is a flow diagram showing an iterative training process for a deep learning/neural network process according to FIG. 2.

In FIG. 4, the procedure 400 generates aty_net: aty_net. This is trained in an iterative, semi-manual semi-automated fashion. An initial set of individual cell images 410 is sorted by human pathologists (step 412), and subsequently used to train an initial neural network (aty_net_1) (420). This network is then used to sort an additional (e.g.) 10,000 images, and its errors are manually corrected by pathologists. This newly sorted data is combined with the previous training set to train a new neural network aty_net_2 (430). The process is repeated until the desired accuracy is reached (i.e. aty_net_n 440).

Figure 5:
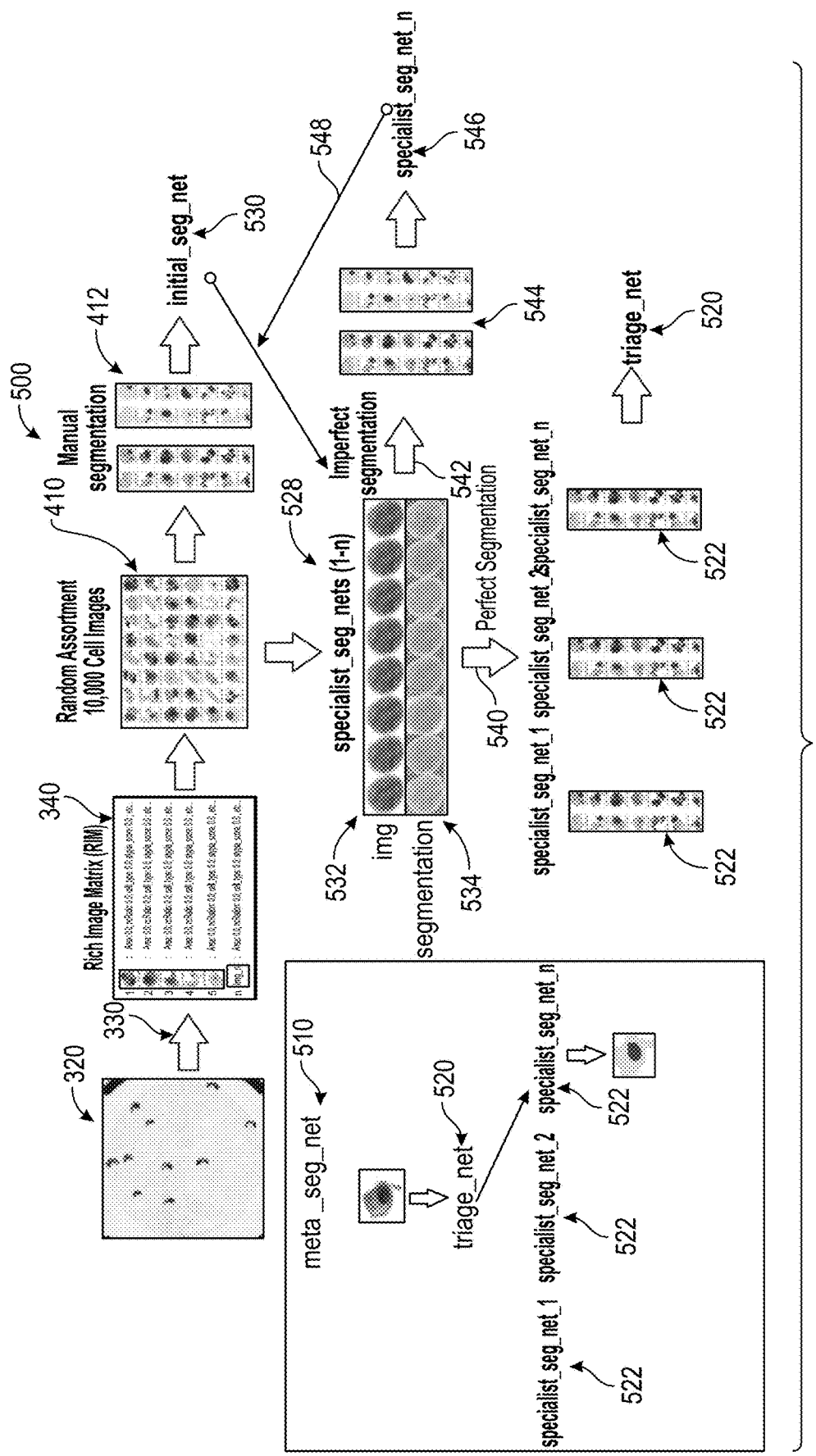
FIG. 5 is a flow diagram showing a semantic segmentation process for classifying incoming images according to FIG. 2.

With reference to FIG. 5, a procedure 500 generates meta_seg_net 510. This is a semantic segmentation procedure composed of a triage neural network 520 and a series of specialist semantic segmentation processes 522. The triage network 520 classifies all incoming images according to the specialist network that is predicted to produce the most accurate segmentation. The networks are trained in an iterative process. Briefly, an initial set of hand segmented images 412 are used to train an initial segmentation network 530. This network is asked to display an original image 532 and 534 along with the predicted segmentation to a pathologist (step 528). The pathologist decides if the segmentation is good (branch 540), in which case the original image is added to the training set for that specialist segmentation network, or bad (branch 542), in which case the image is added to a set of images 544, which need to be manually segmented. The badly segmented images are manually segmented by a pathologist and used to train another specialist segmentation network n (546), at which time it returns (branch 548) to the step 528. A new set of images is shown to the two or more specialist networks, and each produces a predicted segmentation 522, a pathologist decides if it is good or bad and the images are shunted appropriately. This process is repeated until the cohort of specialist segmentation networks segments the majority of images in an acceptable fashion. At this point the original, unsegmented images, which have been added to the good segmentation folder for each specialist network are used to train the triage network 520.

Figure 6:
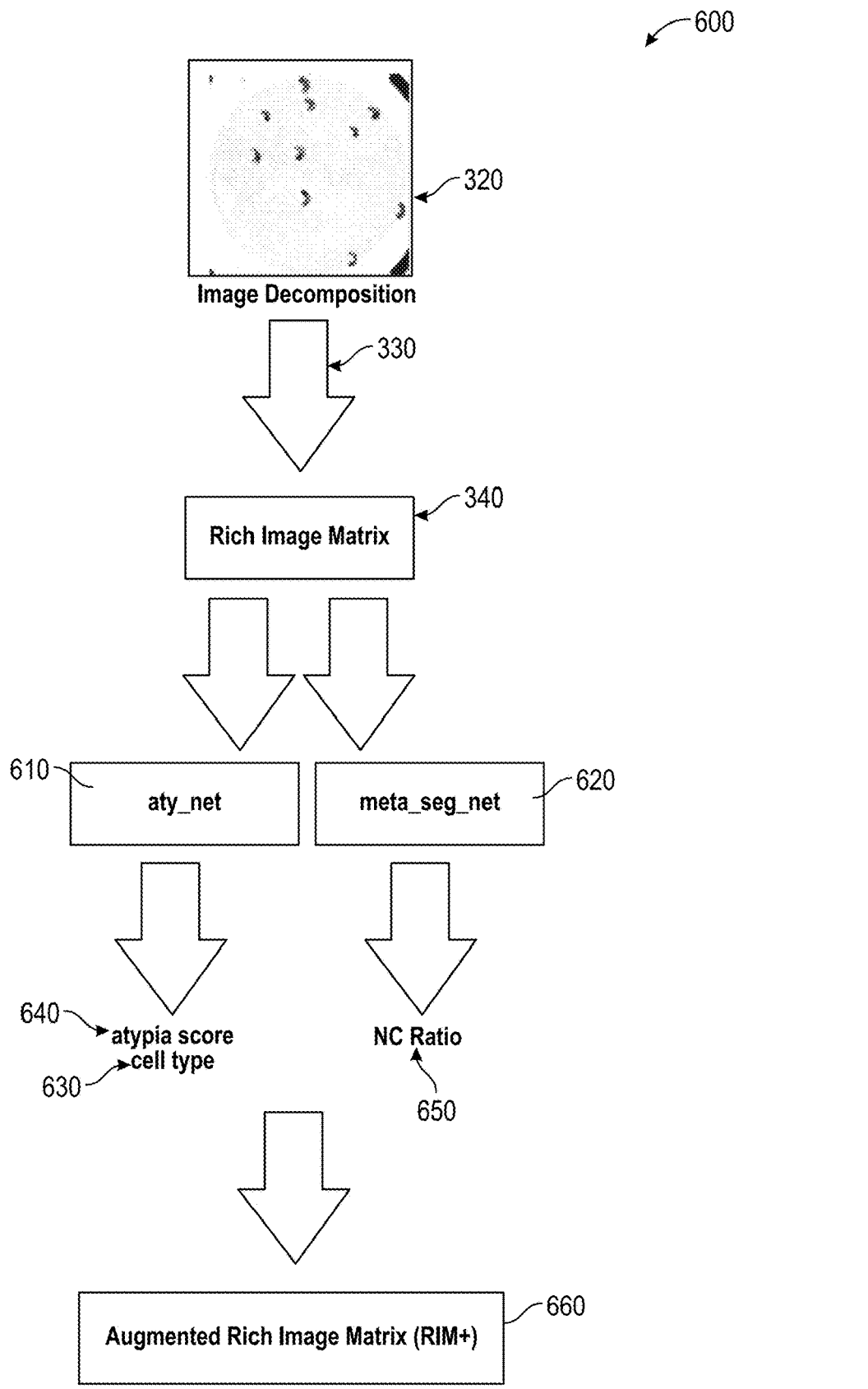
FIG. 6 is a flow diagram showing a procedure for analyzing each cell specified in the RIM to generate and augmented RIM (RIM+) according to FIG. 2.

With reference now to the procedure 600 of FIG. 6, in which RIM and RIM+ are generated. Briefly, every cell in a given RIM 340 is processed by the above-generated aty_net 610 and meta_seg_net 620 to calculate subjective measures such as cell type 630 and atypia score 640 and objective measures such as nuclear to cytoplasmic ratio (NC ratio) 650. These parameters are added to the RIM to create the Augmented RIM (RIM+) 660.

Figure 7:
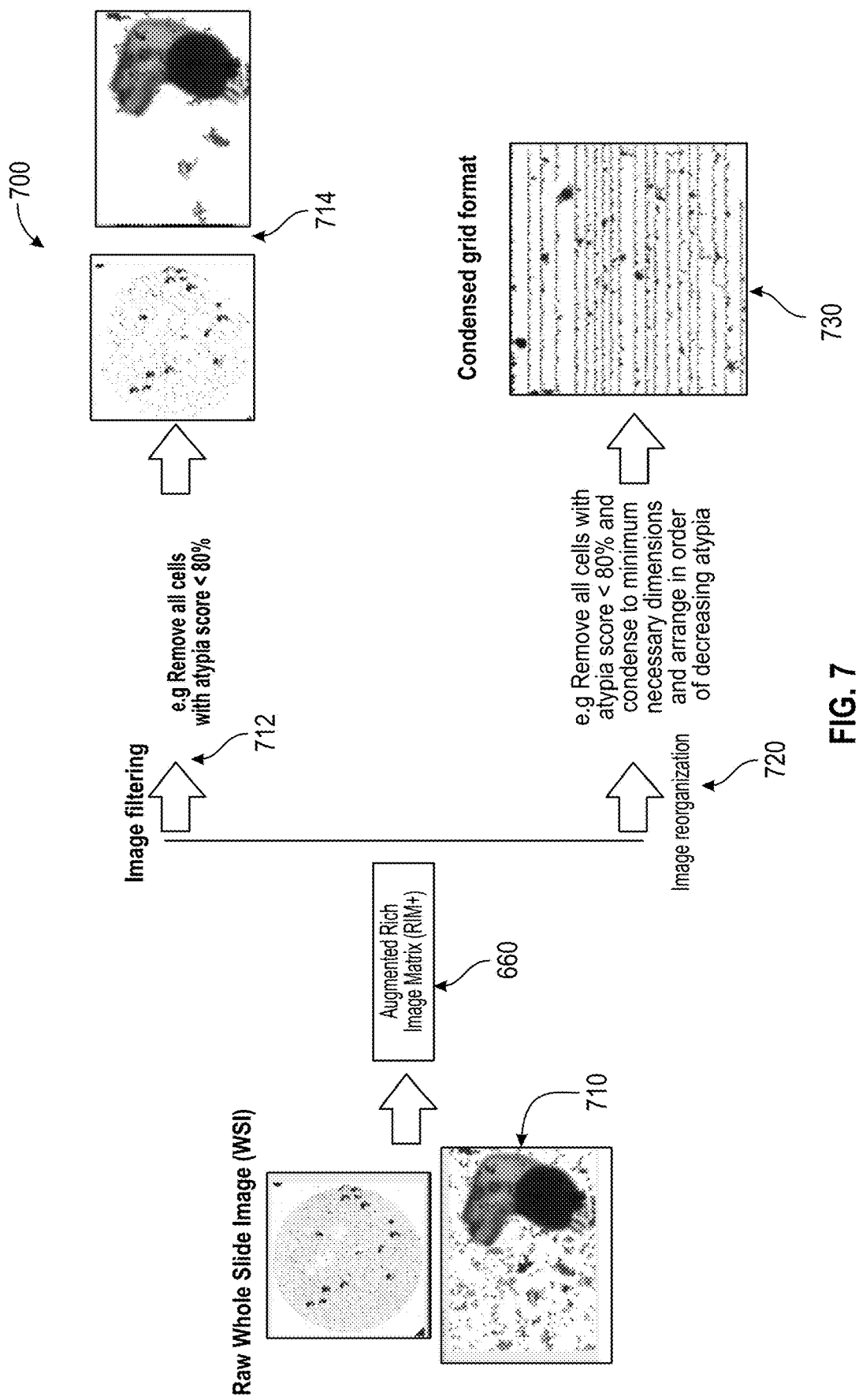
FIG. 7 is a flow diagram showing an image filtering and reorganization procedure for use with the RIM+ generated in FIG. 5, in accordance with the system and method.

Referring now to FIG. 7, the procedure 700 for image filtering and reorganization is shown. Selection and exclusion criteria can be applied to a RIM+ object to either, (a) filter (e.g. remove all blood cells) 712 the original (raw) image 710, thereby generating a filtered image 714; or (b) reorganize 720 the original image 710 to a condensed grid format 730, either with or without filtering. Any number of filtering criteria can be applied in this procedure 700. These results can be delivered to the user during runtime operation as part of an overall information delivery on the sample as described below.

III. Further Considerations for Urine Cytology and Related Procedures

The above-referenced set of procedures can be characterized generally as a hybrid of morphometric and deep learning processes, which can analyze whole slide images (very high resolution scans of slides, WSI) of (e.g.) urine cytopathology specimens and provide a risk score based on analysis of every cell in the entire slide using the criteria of the (e.g.) Paris System as a guide. In this context, the procedures implement four (4) primary tasks:

1. Background deletion and cell identification: The preprocessing algorithm uses thresholding to set background pixels to pure white. It then identifies all contiguous objects separated by white pixels, these are the "cells". A dictionary of every individual cell along with dozens of statistics (cell area, perimeter, average color intensity, location in original image, etc.) is created in the process. This object is the Rich Image Matrix (RIM).

2. Semantic segmentation: A series of deep learning processes are trained to perform a task known as semantic segmentation. In essence these neural networks decide what class each pixel in an image belongs to (cytoplasm, nucleus, background). These neural networks are trained on manually segmented images (images that have been "painted" in the various compartments). The technique can be termed "meta semantic segmentation". Briefly, a series of specialist segmentation networks (e.g. seven networks) is trained to handle various cell morphologies. Images are "shunted" to the proper specialist network by the "triage neural network". The triage network is a different kind of deep learning network which is trained to analyze an incoming cell image and decide which specialist network would produce the best segmentation. Following this analysis, the NC ratio of every cell is determined to a high degree of accuracy (this is Part 1 of the Paris System process).

3. Atypia score: Images of thousands of cells and objects are sorted (by manual, automated and/or semi-automated procedures) to train a neural network to detect and grade atypical urothelial cells. This network (urine_net) analyzes individual cell images from a RIM and produces a prediction of cell type ("atypical urothelial cell", "squamous cell", etc) and an "atypia score" (the score given to the "atypical urothelial cell" category). This atypia score is correlated with the overall likelihood that a given cell represents urothelial carcinoma (this is Part 2 of the Paris System process). This information is added to the RIM object to produce an augmented RIM (RIM+).

Figure 9:
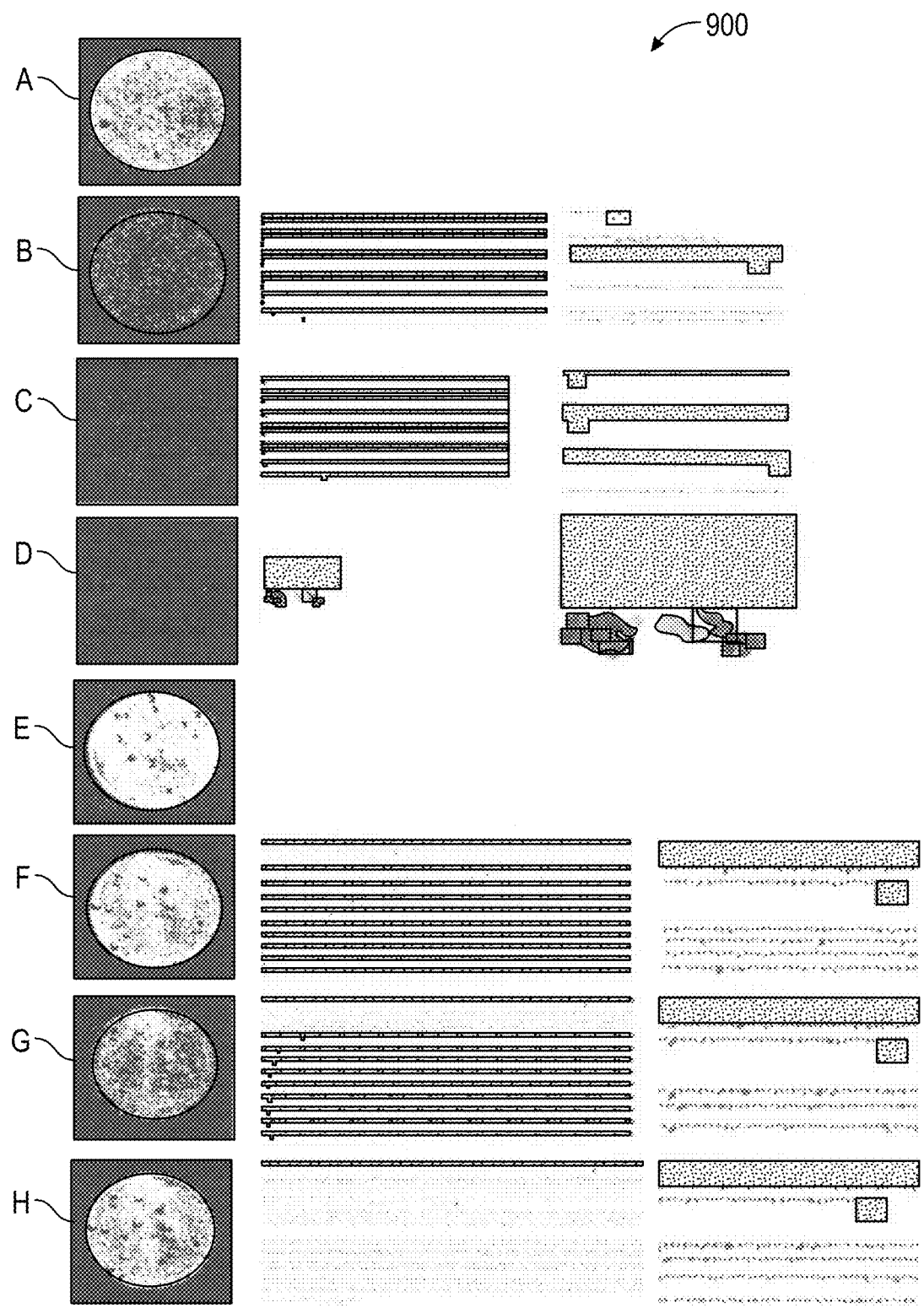
FIG. 9 is a series of variously filtered images based upon the exemplary image of FIG. 8.

4. Image manipulation and pancellular statistics: The RIM+ object contains detailed quantitative and qualitative information about every cell in a given urine WSI. This level of detail is termed "pancellular analysis" herein. Such analysis is effectively unattainable by human and/or manual steps and requires a computing environment to achieve. Many useful manipulations of the data can now be generated for delivery and display to the user. One example is shown in the display(s) 900 of FIG. 9, related to filtering the image to remove extraneous objects (e.g. remove all squamous cells, remove all leukocytes, remove all blood). More particularly, images A-D show negative urine WSI and images E-H show a positive urine WSI (augmented for visibility). Also, A and E are unfiltered. B and F are filtered to contain only urothelial cells (squamous cells, crystals, blood, etc. removed). C and G are filtered to contain only urothelial cells with NC ratio >0.5 (lowest Paris System cutoff for atypia). D and H are filtered to contain only cells with atypia score >90%. To the right are condensed grid format images and zoomed panes from the former. This filtering ability, thus makes the images much less complicated and easier to screen by the user/clinician/specialist.

Figure 8:
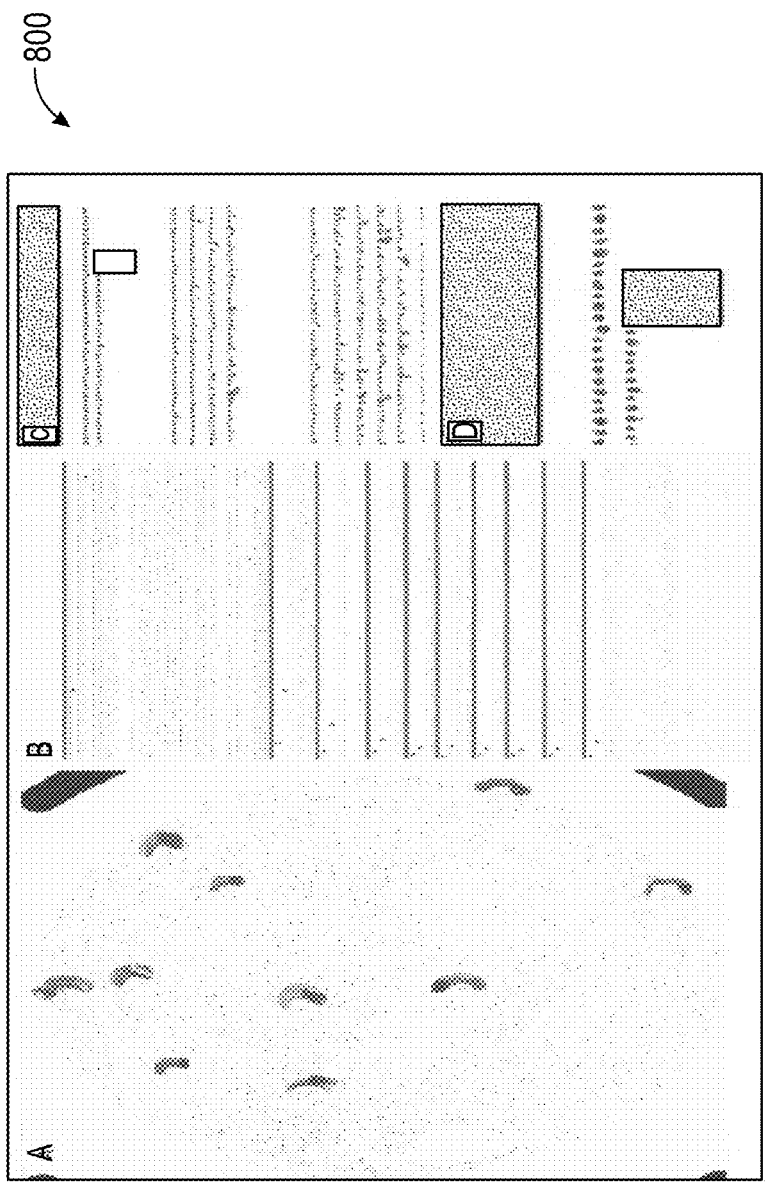
FIG. 8 is an exemplary sample of urine cytology according to the system and method herein showing a whole slide view, a low-magnification decomposed image view, an intermediate magnification decomposed view and a high magnification view of (e.g.) an upper tier of the decomposed view(s)
Figure 10:
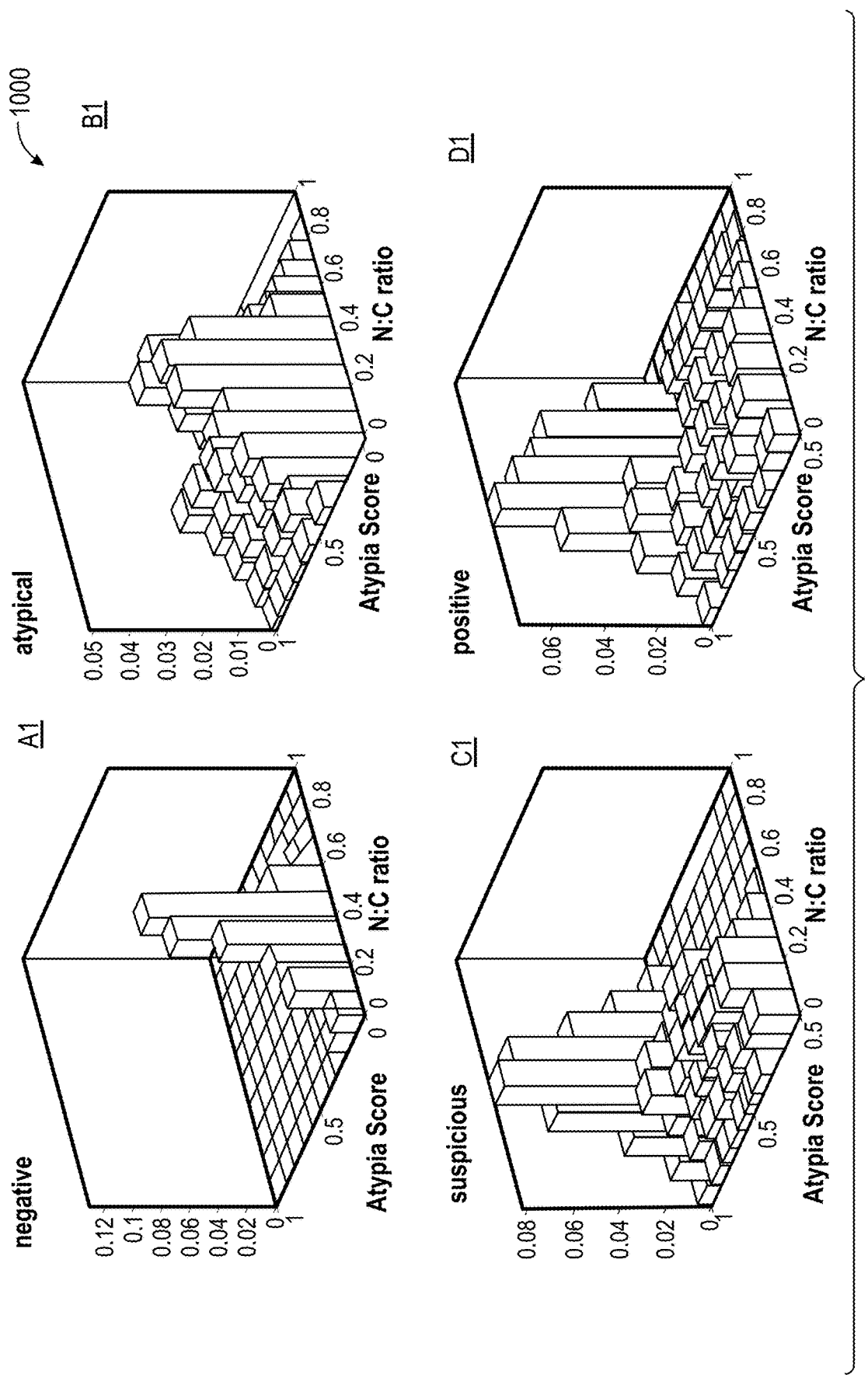
FIG. 10 is a display of an exemplary pancellular analysis of urine cytology that can be delivered to a user of the system and method herein.
Figure 11:
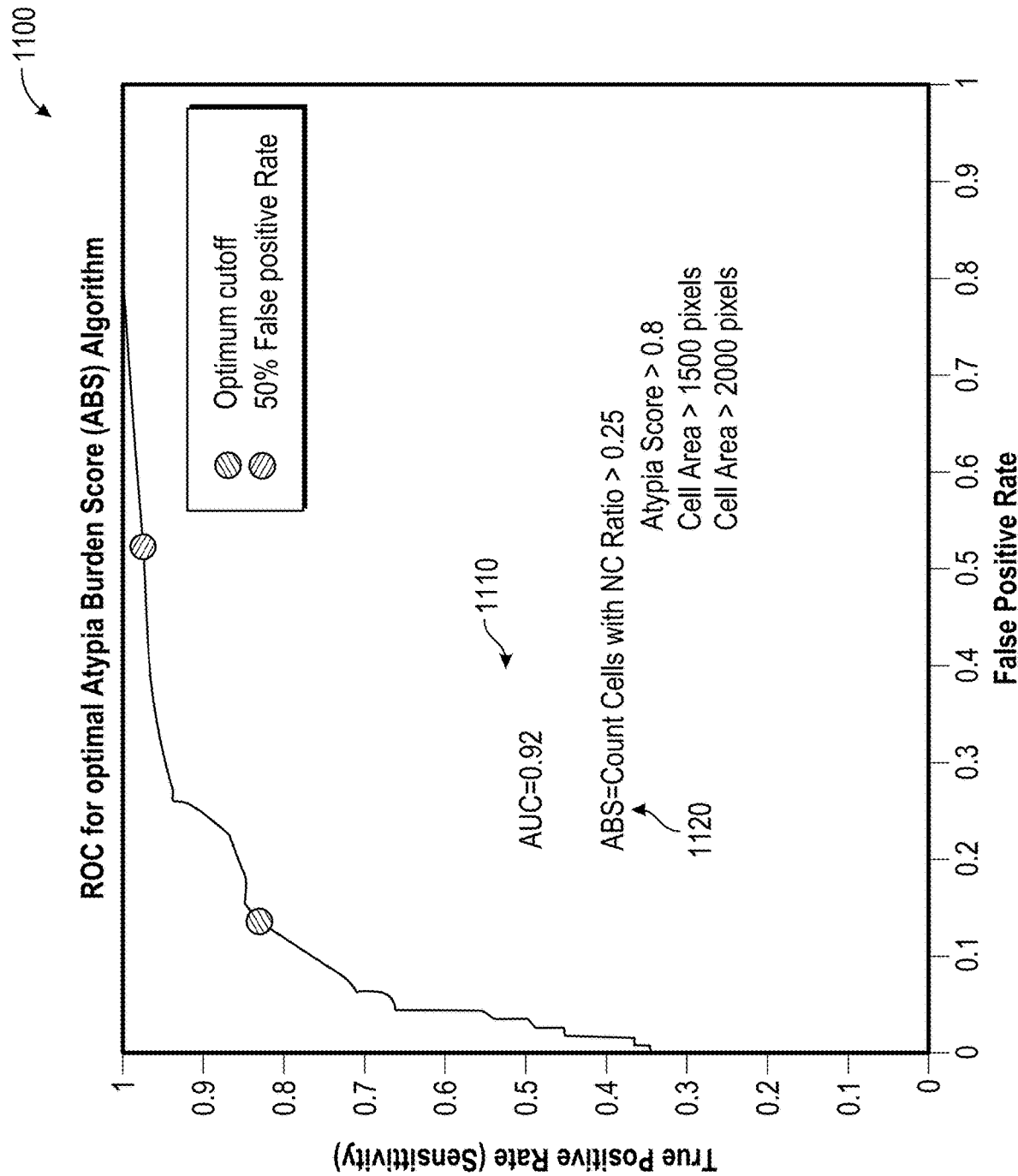
FIG. 11 is a display of an exemplary ROC curve for separating high risk (suspicious and positive) from low risk (atypical and negative) urines that can be delivered to a user of the system and method herein.
Figure 12:
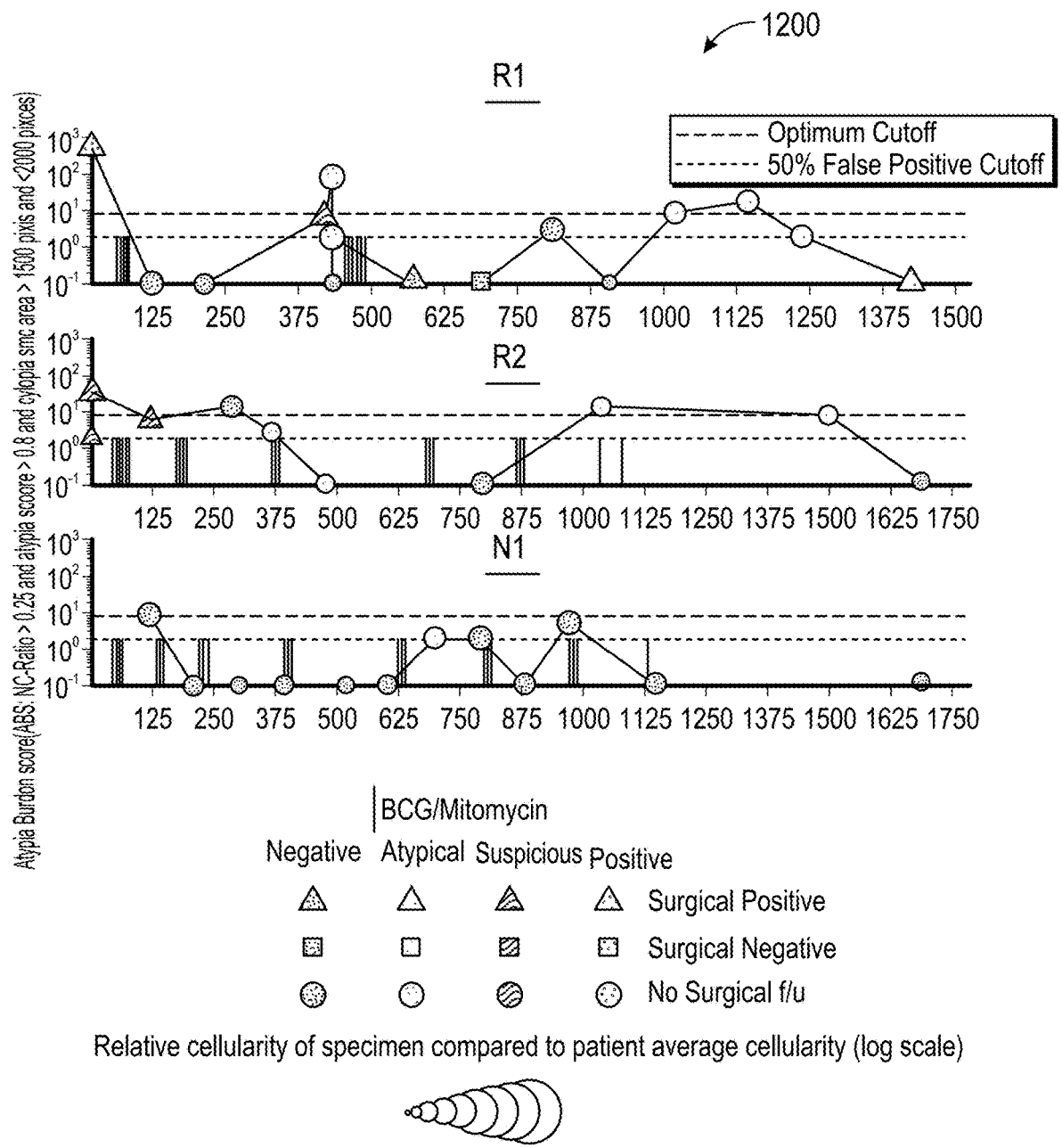
FIG. 12 is a display of an example of atypia burden score (ABS) plotted versus time in days for patients with recurrent urothelial carcinoma and patient without recurrence, which can be delivered to a user of the system and method.

The image can also be rearranged to a "condensed grid" format, which concentrates all cells into a much more compact viewing area. This is shown in the display 800 of FIG. 8, in FIGS. 9 and 10. With reference to FIG. 8, panel A shows a low magnification view of an unmodified whole slide image (WSI, 40× scan) of ThinPrep urine cytopathology specimen with diagnosis of positive for high-grade urothelial carcinoma. Panel B shows a low magnification view of decomposed and reorganized view of the urine WSI depicted in panel A. Each individual cell and cluster has been separated, morphometrically analyzed and scored for atypia by urine_net. The upper tier represents cells and clusters with an atypia score of 90% or more, the next tier contains cells and clusters with atypia score of 80%-<90%, etc. Viewing from left to right, row by row, tier by tier, every cell to the left of a red square has an N:C ratio >=0.7, every cell between a purple square and a red square has an N:C ratio >=0.5 and <0.7, and every cell to the right of a purple square has an N:C ratio <0.5. Panel C shows an intermediate magnification view of upper most tier with detailed view of cluster analysis (small red boxes). Briefly, objects determined to be likely clusters (by nuclear content and area) are segmented and their component parts analyzed by urine_net for atypia. If atypical cells are found within a cluster they are highlighted with a red bounding box and the entire cluster is moved to the tier corresponding to the maximum atypia score in that cluster. Panel D shows a high magnification view of the upper most tier showing the most atypical and highest N:C ratio cells. With reference to FIG. 10, an exemplary display 1000 of pancellular analysis is provided in which aggregate data on cell distributions in 51 negative (A1), 60 atypical (B1), 52 suspicious (C1) and 54 positive (D1) urine whole slide images analyzed by the process. Cells with High NC ratio and high atypia score are more likely to represent urothelial carcinoma. Notably, the pancellular statistics for a given specimen can reveal many interesting facts such as the likelihood of surgically detectable urothelial carcinoma, the risk of recurrence in patients with diagnosis of urothelial carcinoma, the effectiveness of chemotherapy, etc. This is revealed generally in FIGS. 10, 11, and 12. In particular, FIG. 11 shows an exemplary graphical display 1100 of the ROC curve (False Positive Rate versus True Positive Rate), for separating high risk (suspicious and positive) from low risk (atypical and negative) urines by tabulating all cells with NC ratio >0.25 and atypia score >80% and cell area between 1500 and 2000 pixels (to screen out leukocytes). In this example, the optimum cutoff is 9 cells meeting the above criteria with an area under the curve (AUC) of 0.92 (considered excellent for a screening test) 1110. This cutoff is hence referred to as the atypia burden score (ABS) 1120. This exemplary curve was generated by analyzing $1.4 \times 10^7$ cellular objects containing $1.26 \times 10^6$ urothelial cells from 217 total urine RIM+ objects (~50 from each of the four diagnostic categories). FIG. 12 shows an exemplary display 1200 of ABS plotted versus time in days for patients with recurrent urothelial carcinoma (R1, R2), and patient without recurrence (N1). Cytological diagnosis is indicated by the color of the icon at each point (negative, atypical, suspicious, positive equals blue, magenta, yellow, and red, respectively). Triangles indicate surgically proven carcinoma, squares are cases where surgical biopsy did not reveal carcinoma and circles are cases where no surgical biopsy was performed. The size of the icon is proportional to the ratio of cellularity of a given specimen to the patient's average urine cellularity (log scale). Jogs above the red line (optimum cutoff) are concerning for urothelial carcinoma recurrence.

IV. Service Delivery Process

Figure 13:
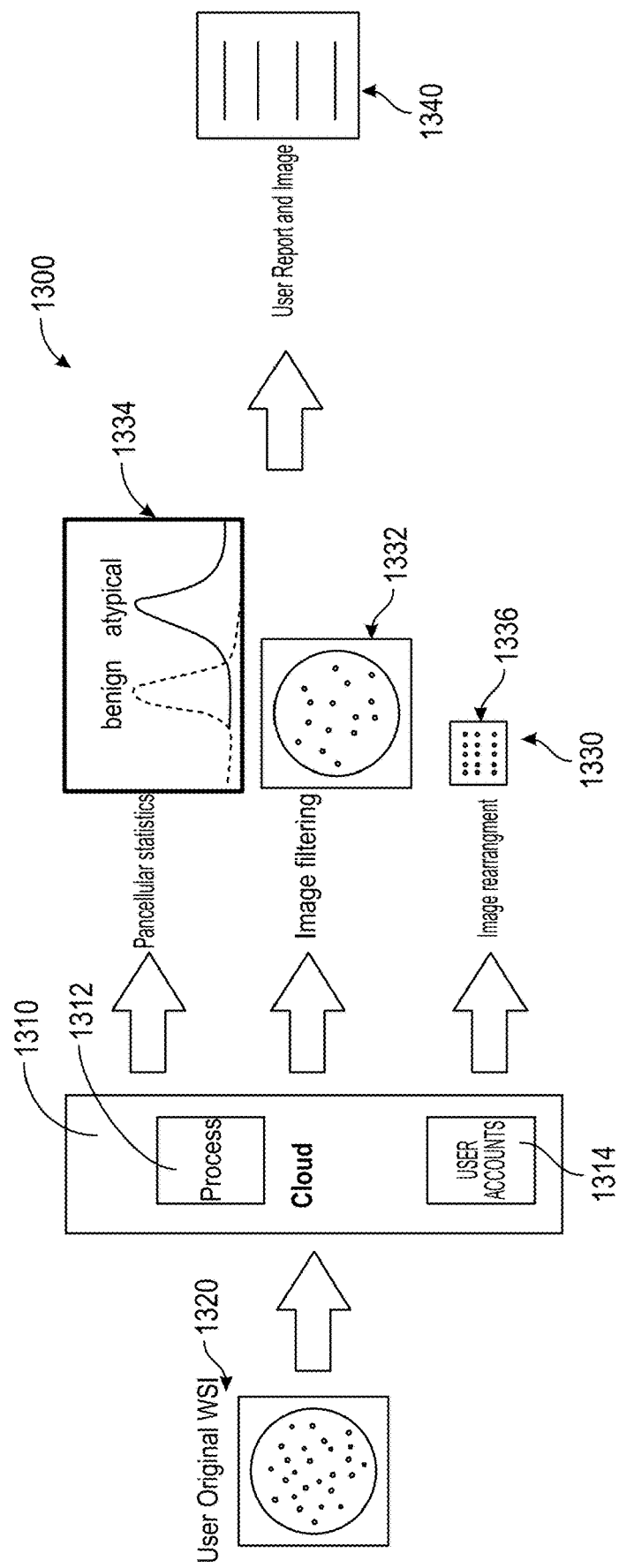
FIG. 13 is a flow diagram showing a service delivery procedure for interacting with users to generate results and manage user accounts according to the system and method.

FIG. 13 shows an exemplary procedure 1300 for delivering service to end users of the system and method herein. In general, the process 1312 resides within the server/cloud environment 1310 as described above. The server/cloud 1310 can also store credentials and subscription/account information for users—for example banking and credit information for use in paying the service as well as identification validation mechanisms (logins, etc.) 1314. Various security protocols, encryption, etc., can also be supported to ensure the confidentiality of data transfers and transactions. In operation, a user acquires a whole slide image and then uploads the whole slide image(s), or relevant image segment(s) 1320. The image(s)/segment(s) are then then be processed by the resident process 1312. The results 1330 returned to the user. These results 1330 can consist of (e.g.) filtered images 1332, risk scores, pancellular statistics 1334, segmented images 1336, etc.). The user can be requested to pay for the computational time and for the services rendered as appropriate to the business model and based upon known billing techniques for such services/resources. In addition the user can elect to fast-track their analysis to a desired degree (e.g. normal processing time, accelerated, STAT, etc.), which can change the overall computation of billed cost. The analysis is then performed and delivered to the user's interface device (1340) on the requisite instance size e.g. (micro, p2.16xlarge, etc.) for a given premium.

V. CONCLUSION

It should be clear that the above-described system and method effectively addresses several disadvantage found in current cytology procedures practiced on urine and other sources of cell tissue. In general, urines are a high volume specimen with poor interobserver diagnostic agreement, and urothelial carcinoma is the most common urological malignancy and, of all cancers, is the most likely to recur (~70%). By effectively automating the tabulation of the Paris Criteria using the system and method herein, the user is provided with a rapid and relatively inexpensive pre-screening of urine cytopathology specimens in a digital format that can be delivered anywhere in the world via telecommunication/Internet connectivity or manual data delivery (disc, thumb drive, etc.). The system and method also allows for the source image to be intelligently manipulated to make screening easier and more efficient. It generates quantitative, completely reproducible data which can provide a "risk score" in what has traditionally been a heavily qualitative practice. Additionally and advantageously, the system and method can be continuously improved and refined by in-line "retraining" of component neural networks with additional data and parameters.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, also as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor here herein can be implemented using electronic hardware, software consisting of a non-transitory computer-readable medium of program instructions, or a combination of hardware and software. Accordingly, this description is meant to be taken only by way of example, and not to otherwise limit the scope of this invention.

What is claimed is:

1. A system comprising:
a whole slide image of a biologic sample stored in a computer accessible data structure;
a cellular detection system executing on a hardware processor that distinguishes between cellular portions and background portions of the biologic sample in the whole slide image;
an atypia neural network executing on one or more processors that produces an atypia score and a cell type for the cellular portions;
a meta segmentation neural network executing on the one or more processors and producing nuclear-to-cytoplasmic ratios of the cellular portions comprising:
  a triage neural network that is trained to determine candidate cell morphology for the cellular portions;
  a set of cell morphology-specific neural networks trained to classify the cellular portions with corresponding candidate cell morphology; and
  the triage neural network configured to select a cell morphology-specific neural network from the set of cell morphology-specific neural networks based on the determined candidate cell morphology, wherein the meta segmentation neural network produces a nuclear-to-cytoplasmic ratio for the cellular portions processed by the selected cell morphology-specific neural network; and
a diagnosis electronic interface that facilitates diagnosis of the biologic sample by presenting pancellular statistics for the cellular portions in a condensed grid of entries representing aggregated data on cell distributions arranged according to atypia score along a first axis and by nuclear-to-cytoplasmic ratio along a second axis.

2. The system of claim 1, wherein the condensed array grid includes entries based on the cell type.

3. The system of claim 1, wherein the cellular detection system decomposes the whole slide image into the cellular portions and background portions.

4. The system of claim 1, wherein the atypia neural network is trained to detect and grade the cellular portions.

5. The system of claim 1, wherein the triage neural network performs the cell morphology-specific neural network selection based on a prediction of segmentation accuracy for each network in the set of cell morphology-specific neural networks.

* * * * *